(12) United States Patent
Long et al.

(10) Patent No.: US 12,220,301 B2
(45) Date of Patent: Feb. 11, 2025

(54) WOUND DRESSINGS AND SYSTEMS WITH THERAPEUTIC GAS AND NEGATIVE PRESSURE SOURCES FOR INCISION MANAGEMENT AND RELATED METHODS

(71) Applicant: Solventum Intellectual Properties Company, Maplewood, MN (US)

(72) Inventors: Justin Alexander Long, San Antonio, TX (US); Christopher Brian Locke, Bournemouth (GB); Kristine M. Kieswfetter, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 1157 days.

(21) Appl. No.: 16/960,940

(22) PCT Filed: Jan. 4, 2019

(86) PCT No.: PCT/US2019/012250
§ 371 (c)(1),
(2) Date: Jul. 9, 2020

(87) PCT Pub. No.: WO2019/139823
PCT Pub. Date: Jul. 18, 2019

(65) Prior Publication Data
US 2021/0001021 A1 Jan. 7, 2021

Related U.S. Application Data (60) Provisional application No. 62/615,718, filed on Jan. 10, 2018.

(51) Int. Cl.
*A61M 1/00* (2006.01)
*A61F 13/05* (2024.01)

(52) U.S. Cl.
CPC ............... *A61F 13/05* (2024.01); *A61M 1/73* (2021.05); *A61M 1/74* (2021.05); *A61M 1/90* (2021.05);
(Continued)

(58) Field of Classification Search
CPC ........... A61F 13/05; A61M 1/73; A61M 1/94; A61M 1/85; A61M 2202/0208; A61M 1/74; A61M 1/90
See application file for complete search history.

(56) References Cited

U.S. PATENT DOCUMENTS 8,372,048 B1 *  2/2013  Azocar ................. A61H 35/00
                                                        604/289
2003/0050674 A1  3/2003  Joshi
(Continued)

FOREIGN PATENT DOCUMENTS

CN       205924317        2/2017
EP       2956101          12/2015
(Continued)

OTHER PUBLICATIONS

International Search Report and Written Opinion issued in Corresponding PCT Application No. PCT/US2019/012250, dated May 7, 2019.
(Continued)

*Primary Examiner* — Susan S Su (57) ABSTRACT

This disclosure includes wound dressings (18) and systems (10) with therapeutic gas and negative pressure sources for incision management. The dressing, which are configured to be coupled to tissue to facilitate delivery of oxygen to the tissue, comprise a manifold configured to permit communication of oxygen to the tissue the manifold (46) defining: a plurality of gas passageways (50); and a plurality of openings (62), one or more of which comprises a length (66) and (Continued)

a width (70) that is at least 50 percent less than the length; and a gas-occlusive layer (86) configured to be disposed over the manifold and coupled to the tissue such that an interior volume containing the manifold is defined between the gas-occlusive layer and the tissue and the gas-occlusive layer limits escape of oxygen from the interior volume.

8 Claims, 5 Drawing Sheets

(52) U.S. Cl.
CPC .............. *A61M 1/94* (2021.05); *A61M 1/962* (2021.05); *A61M 1/964* (2021.05); *A61M 1/85* (2021.05); *A61M 2202/0208* (2013.01); *A61M 2205/3324* (2013.01); *A61M 2205/7536* (2013.01); *A61M 2205/8206* (2013.01); *A61M 2205/8243* (2013.01)

(56) References Cited

U.S. PATENT DOCUMENTS

| | | | |
|---|---|---|---|
| 2004/0030304 A1* | 2/2004 | Hunt | A61L 15/425 604/317 |
| 2004/0260253 A1 | 12/2004 | Rosati | |
| 2005/0022810 A1* | 2/2005 | Moore | A61M 16/0078 128/202.26 |
| 2006/0200100 A1 | 9/2006 | Rosati | |
| 2009/0227969 A1 | 9/2009 | Jaeb et al. | |
| 2009/0259171 A1 | 10/2009 | Joshi et al. | |
| 2010/0069858 A1 | 3/2010 | Olson | |
| 2010/0305490 A1 | 12/2010 | Coulthard et al. | |
| 2012/0059301 A1 | 3/2012 | Franklin | |
| 2012/0209226 A1 | 8/2012 | Simmons et al. | |
| 2016/0030722 A1 | 2/2016 | Anderson et al. | |
| 2016/0166781 A1 | 6/2016 | Sarangapani et al. | |
| 2016/0175500 A1 | 6/2016 | Cali et al. | |
| 2017/0319394 A1 | 11/2017 | Chen et al. | |
| 2020/0121510 A1* | 4/2020 | Hartwell | A61M 1/94 |

FOREIGN PATENT DOCUMENTS

| | | |
|---|---|---|
| TW | 200942281 | 10/2009 |
| TW | M525742 | 7/2016 |
| WO | WO 1996/032082 | 10/1996 |
| WO | WO 2009/066106 | 5/2009 |
| WO | WO 2009/097534 | 8/2009 |
| WO | WO 2009/146441 | 12/2009 |
| WO | WO 2009/158500 | 12/2009 |
| WO | WO 2011/008497 | 1/2011 |
| WO | WO 2011/008711 | 1/2011 |
| WO | WO 2013/066694 | 5/2013 |
| WO | WO 2014/144762 | 9/2014 |
| WO | WO 2015/123353 | 8/2015 |

OTHER PUBLICATIONS

International Search Report and Written Opinion issued in Corresponding PCT Application No. PCT/US2018/051408, dated Jan. 23, 2019.
International Search Report and Written Opinion issued in Corresponding PCT Application No. PCT/US2018/052137, dated Dec. 19, 2018.
International Search Report and Written Opinion issued in Corresponding PCT Application No. PCT/US2019/012273, dated May 16, 2019.
International Search Report and Written Opinion Issued in Corresponding PCT Patent Application No. PCT/US2018/057214, dated Jan. 31, 2019.

* cited by examiner

WOUND DRESSINGS AND SYSTEMS WITH THERAPEUTIC GAS AND NEGATIVE PRESSURE SOURCES FOR INCISION MANAGEMENT AND RELATED METHODS

CROSS-REFERENCE TO RELATED APPLICATIONS

This application is a national phase application under 35 U.S.C. § 371 of International Application No. PCT/US2019/012250, filed Jan. 4, 2019, which claims priority to and the benefit of U.S. Provisional Application No. 62/615,718, filed Jan. 10, 2018. The contents of the referenced patent applications are incorporated into the present application in their entirety.

BACKGROUND

1. Field of Invention

The present invention relates generally to wound dressings, and more specifically, but not by way of limitation, to wound dressings and systems with therapeutic gas and negative pressure sources for incision management and related methods.

2. Description of Related Art

Traditional negative pressure-based wound therapies for surgical wounds require the use of active antimicrobial agents, such as silver nanocrystals, to minimize the risk of bacterial colonization of a wound dressing. However, the use of silver as an antimicrobial agent can be contraindicated for individuals with a metal allergy.

Thus, while the clinical benefits of negative pressure-based wound therapies with silver nanocrystals for surgical wounds are known, improvements to the applicability, convenience, and/or simplicity of therapy systems, components, and related methods with active antimicrobial agents other than silver may benefit healthcare providers, caregivers, and patients.

SUMMARY

Benefits of the present dressings, systems, and/or methods include reducing risks of dehiscence and bolstering incisional wound margins by applying negative pressure wound therapy to a wound. Additional benefits include the removal of fluid from the wound, providing an occlusive, sterile barrier to protect against infection, and boosting the body's own defense against surgical wound site infections and increasing collagen formation, which can reduce the appearance of scarring, by delivering a high concentration of therapeutic oxygen to the wound site. Further benefits include the ability to sterilize and/or replace a dressing without disturbing a negative pressure and/or oxygen source at least because the negative pressure and oxygen source are decouplable from the dressing. The present dressings, systems, and/or methods also allow for safely discarding a dressing as medical waste and recycle and/or discarding a negative pressure and/or oxygen source according to Waste Electrical and Electronic Equipment (WEEE) recycling standards at least because the negative pressure and oxygen source are decouplable from the dressing. The ability for a patient to remove a negative pressure and/or oxygen source from a dressing without removing the dressing from tissue allows remote recharging of the negative pressure and/or oxygen source and/or allows an individual access into areas where metals and/or electronics are prohibited (e.g., MRI scanning, metal detectors, and/or the like). By providing the ability to decouple a dressing from a negative pressure and/or oxygen source, a single negative pressure source can be removed and reused on multiple dressings, which can be useful where a wound is more highly exudating and a dressing becomes saturated before negative pressure therapy is completed. Finally, the present dressings, systems, and methods can facilitate the ability to omit a conventional on/off switch and instead provide remote-controlled actuation of negative pressure and/or oxygen therapy upon application of the system to tissue at least until the removal of the system or, in some instances, the depletion of a finite power source.

Some embodiments of the present systems comprise a dressing for facilitating delivery of oxygen to tissue, the dressing comprising: a manifold that defines a plurality of gas passageways and is configured to permit communication of oxygen to the target tissue; a gas-occlusive layer configured to be disposed over the manifold and coupled to the tissue such that an interior volume containing the manifold is defined between the gas-occlusive layer and the tissue and the gas-occlusive layer limits escape of oxygen from the interior volume; a housing outside the interior volume, the housing having a sidewall that defines a chamber configured to be in fluid communication with the interior volume; an oxygen source disposed within the chamber, the oxygen source configured to be in fluid communication with the interior volume; and a negative pressure source disposed within the chamber, the negative pressure source configured to be in fluid communication with the interior volume such that the negative pressure source provides sub-atmospheric pressure within the interior volume.

In some embodiments of the present systems, the manifold defines a plurality of openings, one or more of which comprises a length and a width that is at least 50 percent less than the length.

In some embodiments of the present systems, the negative pressure source comprises one or more elements selected from the group consisting of: a piezoelectric disc pump, a diaphragm pump, and a rotary vane pump.

Some embodiments of the present systems comprises a power source disposed within the chamber and configured to provide power to actuate the negative pressure source and/or the oxygen source. In some embodiments of the present systems, the power source comprises a primary cell battery. In some embodiments of the present systems, the power source comprises a secondary cell battery. In some embodiments of the present systems, the secondary cell battery is configured to be inductively charged through the sidewall of the housing.

Some embodiments of the present systems comprise a controller configured to control the power provided by the power source to the negative pressure source and/or the oxygen source.

In some embodiments of the present systems, the oxygen source is configured to provide oxygen at a volumetric flow rate ranging from approximately 3 milliliters per hour (mL/hr) to approximately 50 mL/hr. In some embodiments of the present systems, the oxygen source is configured to provide oxygen at a purity of at least 90 percent. In some embodiments of the present systems, the oxygen source comprises an electrolytic oxygen source.

Some embodiments of the present systems comprising a second oxygen source disposed within the interior volume, the second oxygen source having an oxygen-generating material configured to release oxygen when exposed to a liquid. In some embodiments of the present systems, the oxygen-generating material comprises an adduct of hydrogen peroxide. In some embodiments of the present systems, the adduct comprises sodium percarbonate and/or hydrogen peroxide-urea. In some embodiments of the present systems, the interior volume includes one or more capsules, each of which define a pocket that includes a liquid.

Some embodiments of the present systems comprises a port coupled to the gas-occlusive layer and configured to be releasably coupled to the housing to permit communication of fluid between the chamber and the interior volume through the port. In some embodiments of the present systems, the port is configured to permit communication of oxygen into the interior volume through the port and permit communication of exudate out of the interior volume through the port.

In some embodiments of the present systems, the dressing comprises a filter configured to filter fluid that flows through the port. In some embodiments of the present systems, the filter comprises a layer of material that is bonded to an upper surface or a lower surface of the gas-occlusive layer. In some embodiments of the present systems, the filter is configured to permit communication of oxygen into the interior volume through the port and restrict communication of exudate out of the interior volume through the port. In some embodiments of the present systems, the filter is configured to provide a viral and/or bacterial barrier.

In some embodiments of the present systems, the housing comprises a port coupled to the sidewall and configured to be releasably coupled to the port of the dressing such that the housing can be decoupled from the dressing without decoupling the dressing from the tissue.

Some embodiments of the present systems comprises a valve coupled to the gas-occlusive layer of the dressing and configured to relieve pressure within the interior volume when pressure within the interior volume exceeds a threshold pressure. In some embodiments of the present systems, the valve comprises a one-way valve configured to: permit communication of gas out of the interior volume through the valve; and prevent communication of gas into the interior volume through the valve.

Some embodiments of the present systems comprises a patient-interface layer configured to be disposed within the interior volume and to be in contact with the tissue surrounding the target tissue, the patient-interface layer defining a plurality of openings configured to permit communication of oxygen and exudate through the patient-interface layer.

Some embodiments of the present systems comprises a sorbent material configured to be disposed above or below the manifold and to capture exudate. In some embodiments of the present systems, the sorbent material comprises an absorbent material. In some embodiments of the present systems, the sorbent material comprises an adsorbent material.

In some embodiments of the present systems, the patient-interface layer comprises a polymer, optionally, silicone, polyethylene, ethylene vinyl acetate, a copolymer thereof, or a blend thereof. In some embodiments of the present systems, the patient-interface layer includes an adhesive configured to couple the patient-interface layer to the tissue.

In some embodiments of the present systems, the manifold comprises a foam or a non-woven textile. In some embodiments of the present systems, the manifold comprises polyethylene, a polyolefin, a polyether, polyurethane, a co-polyester, a copolymer thereof, or a blend thereof.

In some embodiments of the present systems, the gas-occlusive layer comprises polyurethane, polyethylene, polyvinyl acetate, polyvinyl chloride, polyvinylidene chloride, isobutylene, a halogenated isomer, a copolymer thereof, or a blend thereof. In some embodiments of the present systems, the gas-occlusive layer comprises an adhesive configured to couple the gas-occlusive layer to tissue surrounding the target tissue. In some embodiments of the present systems, the adhesive comprises an acrylic adhesive, polyurethane gel adhesive, silicone adhesive, or a combination thereof.

In some embodiments of the present systems, the sidewall of the housing is gas-occlusive. In some embodiments of the present systems, the sidewall comprises polyurethane, polyethylene, polyvinyl acetate, polyvinyl chloride, polyvinylidene chloride, isobutylene, a halogenated isomer, a copolymer thereof, or a blend thereof.

Some embodiments of the present dressings, which are configured to be coupled to tissue to facilitate delivery of oxygen to the tissue, comprise: a manifold configured to permit communication of oxygen to the tissue, the manifold defining: a plurality of gas passageways; and a plurality of openings, one or more of which comprises a length and a width that is at least 50 percent less than the length; and a gas-occlusive layer configured to be disposed over the manifold and coupled to the tissue such that an interior volume containing the manifold is defined between the gas-occlusive layer and the tissue and the gas-occlusive layer limits escape of oxygen from the interior volume.

Some embodiments of the present dressings comprise a port coupled to the gas-occlusive layer, wherein the port is configured to be releasably coupled to a port of a housing having a sidewall defining a chamber to permit communication of fluid between the chamber and the interior volume through the ports.

Some embodiments of the present dressings, which are configured to be coupled to tissue to facilitate delivery of oxygen to the tissue, comprise: a manifold that defines a plurality of gas passageways and is configured to permit communication of oxygen to the tissue; a gas-occlusive layer configured to be disposed over the manifold and coupled to the tissue such that an interior volume containing the manifold is defined between the gas-occlusive layer and the tissue and the gas-occlusive layer limits escape of oxygen from the interior volume; and a port coupled to the gas-occlusive layer, wherein the port is configured to be releasably coupled to a port of a housing having a sidewall defining a chamber to permit communication of fluid between the chamber and the interior volume through the ports.

In some embodiments of the present dressings, the manifold defines a plurality of openings, one or more of which comprises a length and a width that is at least 50 percent less than the length.

In some embodiments of the present dressings, the housing is configured to include an oxygen source disposed within the chamber, the oxygen source configured to be in fluid communication with the interior volume such that the oxygen source provides oxygen at a volumetric flow rate ranging from approximately 3 milliliters per hour (mL/hr) to approximately 50 mL/hr.

In some embodiments of the present dressings, the oxygen source is configured to provide oxygen at a purity of at least 90 percent. In some embodiments of the present dressings, the oxygen source comprises an electrolytic oxygen source.

Some embodiments of the present dressings comprise a second oxygen source disposed within the interior volume, the second oxygen source having an oxygen-generating material configured to release oxygen when exposed to a liquid. In some embodiments of the present dressings, the oxygen-generating material comprises an adduct of hydrogen peroxide. In some embodiments of the present dressings, the adduct comprises sodium percarbonate and/or hydrogen peroxide-urea. Some embodiments of the present dressings comprise a competitive agent disposed within the interior volume, the competitive agent configured to limit the communication of oxygen to the tissue. In some embodiments of the present dressings, competitive agent includes sodium carbonate. In some embodiments of the present dressings, the interior volume includes one or more capsules, each of which defines a pocket that includes a liquid. In some embodiments of the present dressings, flexion of a portion of at least one of the one or more capsules causes the capsule to release liquid from within the pocket.

In some embodiments of the present dressings, the housing is configured to include a negative pressure source disposed within the chamber, the negative pressure source configured to be in fluid communication with the interior volume such that the negative pressure source provides sub-atmospheric pressure within the interior volume. In some embodiments of the present dressings, the negative pressure source comprises one or more elements selected from the group consisting of: a piezoelectric disc pump, a diaphragm pump, and a rotary vane pump.

In some embodiments of the present dressings, the port of the dressing is configured to permit communication of oxygen into the interior volume through the port and permit communication of exudate out of the interior volume through the port. Some embodiments of the present dressings comprise a filter configured to filter fluid that flows through the port. In some embodiments of the present dressings, the filter comprises a layer of material that is bonded to an upper surface or a lower surface of the gas-occlusive layer. In some embodiments of the present dressings, the filter is configured to permit communication of oxygen into the interior volume through the port and restrict communication of exudate out of the interior volume through the port. In some embodiments of the present dressings, the filter is configured to provide a viral and/or bacterial barrier.

Some embodiments of the present dressings comprise a valve coupled to the gas-occlusive layer and configured to relieve pressure within the interior volume when pressure within the interior volume exceeds a threshold pressure. In some embodiments of the present dressings, the valve comprises a one-way valve configured to: permit communication of gas out of the interior volume through the valve; and prevent communication of gas into the interior volume through the valve.

Some embodiments of the present dressings comprises a patient-interface layer configured to be disposed below the manifold and in contact with the tissue, the patient-interface layer defining a plurality of openings configured to permit communication of oxygen and exudate through the patient-interface layer.

Some embodiments of the present dressings comprises a sorbent material configured to be disposed above or below the manifold and to capture exudate. Some embodiments of the present dressings comprises a sorbent layer that includes the sorbent material. In some embodiments of the present dressings, the sorbent material comprises an absorbent material. In some embodiments of the present dressings, the sorbent material comprises an adsorbent material.

In some embodiments of the present dressings, the patient-interface layer comprises a polymer, optionally, silicone, polyethylene, ethylene vinyl acetate, a copolymer thereof, or a blend thereof. In some embodiments of the present dressings, the patient-interface layer includes an adhesive configured to couple the patient-interface layer to the tissue.

In some embodiments of the present dressings, the manifold comprises a foam or a non-woven textile. In some embodiments of the present dressings, the manifold comprises polyethylene, a polyolefin, a polyether, polyurethane, a co-polyester, a copolymer thereof, or a blend thereof.

In some embodiments of the present dressings, the gas-occlusive layer comprises polyurethane, polyethylene, polyvinyl acetate, polyvinyl chloride, polyvinylidene chloride, isobutylene, a halogenated isomer, a copolymer thereof, or a blend thereof. In some embodiments of the present dressings, the gas-occlusive layer comprises an adhesive configured to couple the gas-occlusive layer to the tissue. In some embodiments of the present dressings, the adhesive comprises an acrylic adhesive, polyurethane gel adhesive, silicone adhesive, or a combination thereof.

Some embodiments of the present dressings comprises a sensor configured to detect a presence of oxygen within the interior volume. In some embodiments of the present dressings, the sensor comprises a material configured to be disposed within the interior volume and to change color in response to a change in oxygen concentration within the interior volume. In some embodiments of the present dressings, the material comprises a pressure-sensitive paint. In some embodiments of the present dressings, the material comprises a redox indicator. In some embodiments of the present dressings, the redox indicator comprises methylene blue, phenosafranine, indigo carmine, resazurin, N-phenylanthranilic acid, and/or neutral red. In some embodiments of the present dressings, the material is disposed on a lower surface of the gas-occlusive layer. In some embodiments of the present dressings, the sensor comprises: a layered silicate; a cationic surfactant; an organic colorant; and a reducing agent.

Some embodiments of the present methods comprise coupling the dressing of any the embodiments described herein to a patient's tissue; and coupling a housing to the dressing, wherein the housing comprises: a sidewall that defines a chamber configured to be in fluid communication with the interior volume; an oxygen source disposed within the chamber, the oxygen source configured to be in fluid communication with the interior volume; and a negative pressure source disposed within the chamber, the negative pressure source configured to be in fluid communication with the interior volume such that the negative pressure source provides sub-atmospheric pressure within the interior volume.

Some embodiments of the present methods comprise introducing oxygen from the oxygen source into the interior volume. In some embodiments of the present methods, introducing oxygen into the interior volume is performed at a volumetric flow rate ranging from approximately 3 milliliters per hour (mL/hr) to approximately 50 mL/hr. In some embodiments of the present methods, oxygen introduced into the interior volume is at a purity of at least 90 percent. In some embodiments of the present methods, oxygen introduced into the interior volume is produced via electrolysis.

In some embodiments of the present methods, the dressing is configured to include a second oxygen source within the interior volume, the second oxygen source having an oxygen-generating material and the method comprises introducing oxygen from the second oxygen source into the interior volume. In some embodiments of the present methods, oxygen introduced from the second oxygen source into the interior volume is produced by exposing the oxygen-generating material to a liquid. In some embodiments of the present methods, the oxygen-generating material comprises an adduct of hydrogen peroxide. In some embodiments of the present methods, the adduct comprises sodium percarbonate and/or hydrogen peroxide-urea.

Some embodiments of the present methods comprise applying sub-atmospheric pressure within the interior volume. In some embodiments of the present methods, the sub-atmospheric pressure is applied to and oxygen is introduced into the interior volume simultaneously.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The phrase "and/or" means and or. The phrase "and/or" includes any and all combinations of one or more of the associated listed items. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes," one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Further, an apparatus that is configured in a certain way is configured in at least that way, but it can also be configured in other ways than those specifically described.

Some details associated with the embodiments are described above, and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures. Figures having schematic views are not drawn to scale.

DETAILED DESCRIPTION

Figure 1:
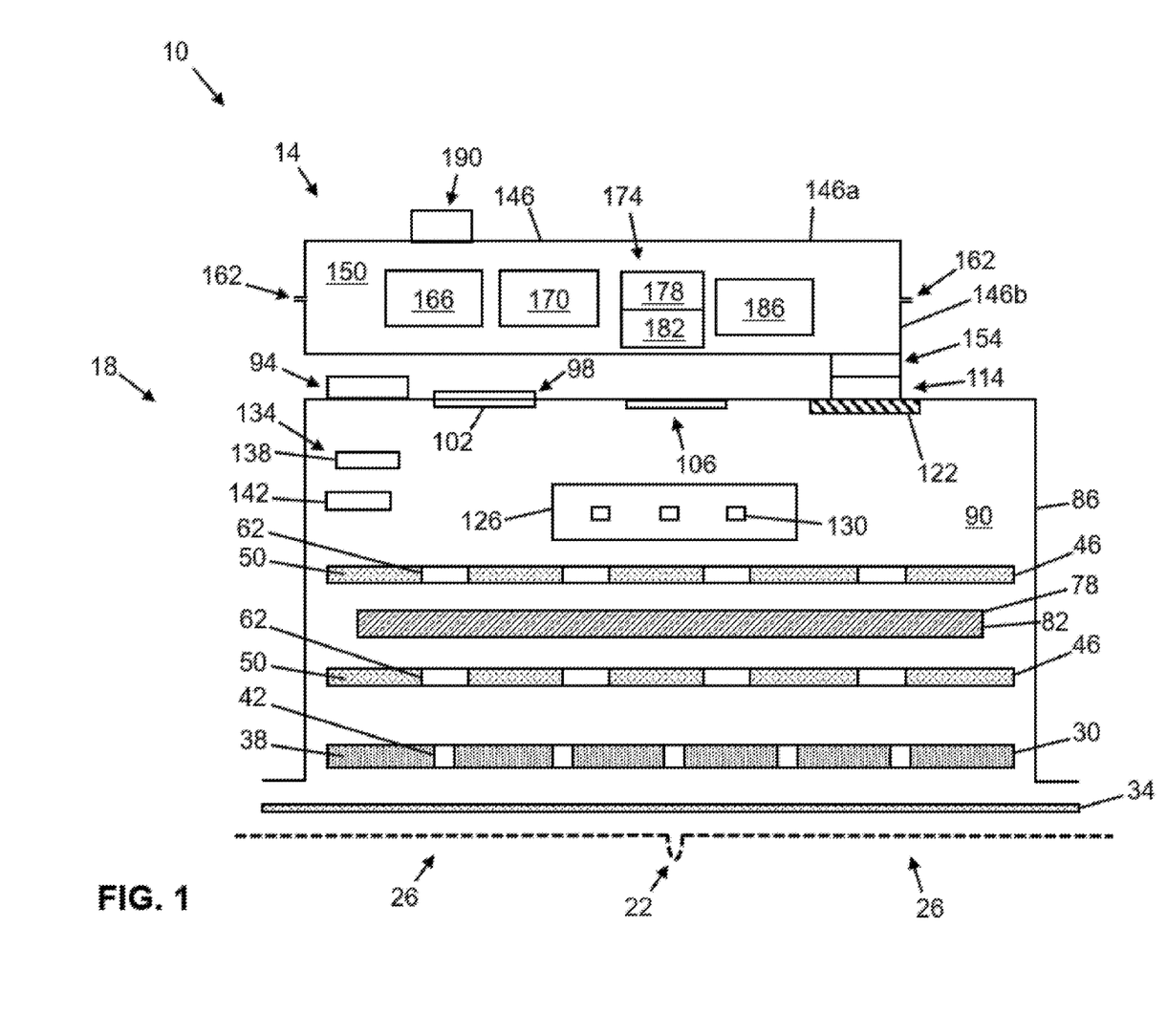
FIG. 1 is a schematic view of an embodiment of the present systems.

Referring to FIG. 1, shown therein and designated by the reference numeral 10 is one embodiment of the present systems for providing negative pressure and topical wound therapy. System 10 includes a therapy housing 14 configured to be coupled to a wound dressing 18. Dressing 18 is configured to be coupled to target tissue 22 and/or to tissue 26 surrounding the target tissue to facilitate delivery of therapeutic gas, such as, for example, oxygen, and/or negative pressure to the target tissue.

The term "target tissue" as used herein can broadly refer to an open wound located within tissue, such as, for example, dermal tissue. The term "wound" as used herein can refer to a chronic, subacute, acute, traumatic, and/or dehisced incision, laceration, puncture, penetration, avulsion, and/or the like.

Figure 2:
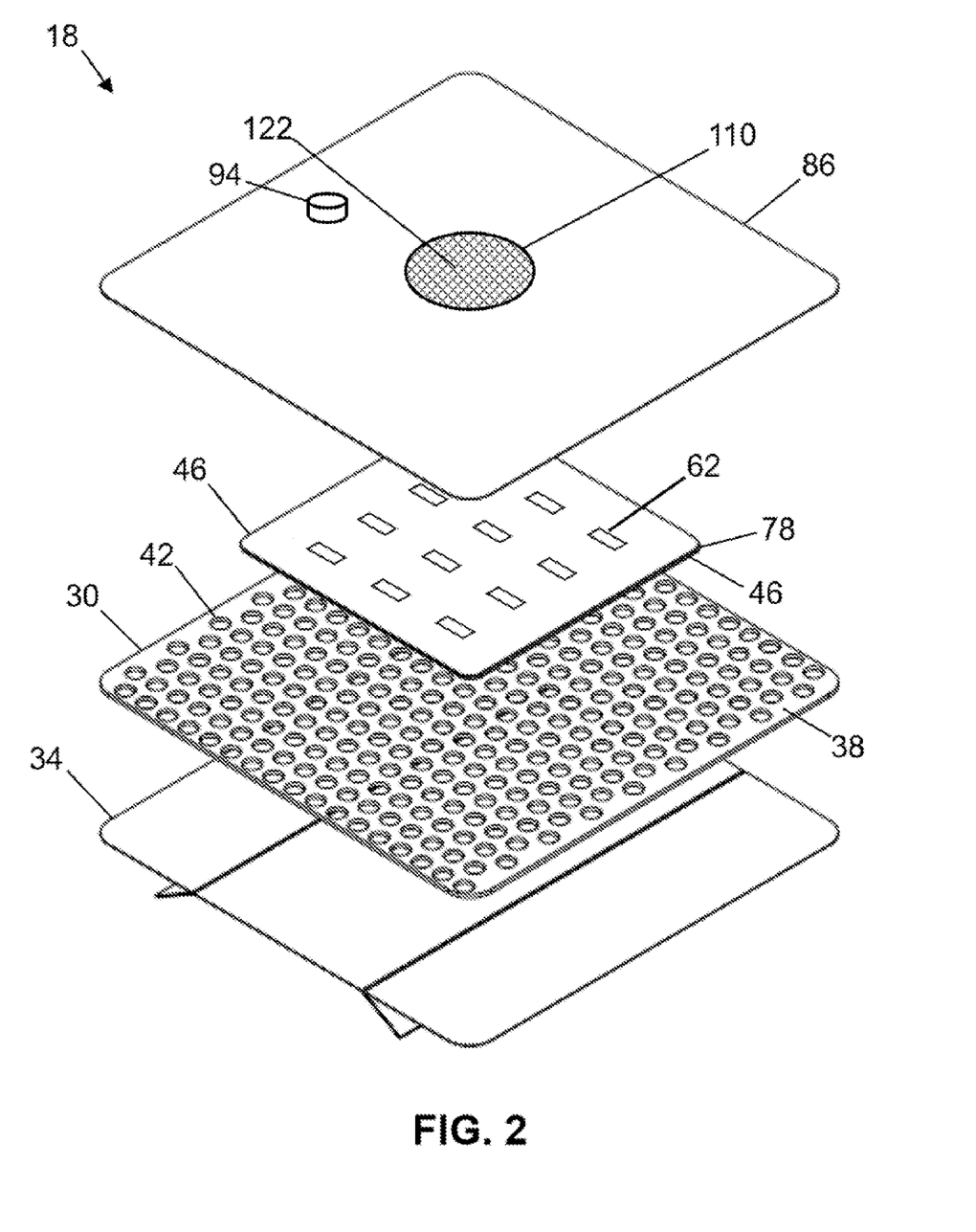
FIG. 2 is an exploded perspective view of a first embodiment of the present wound dressings, suitable for use in some embodiments of the present systems, shown with some components omitted.
Figure 3:
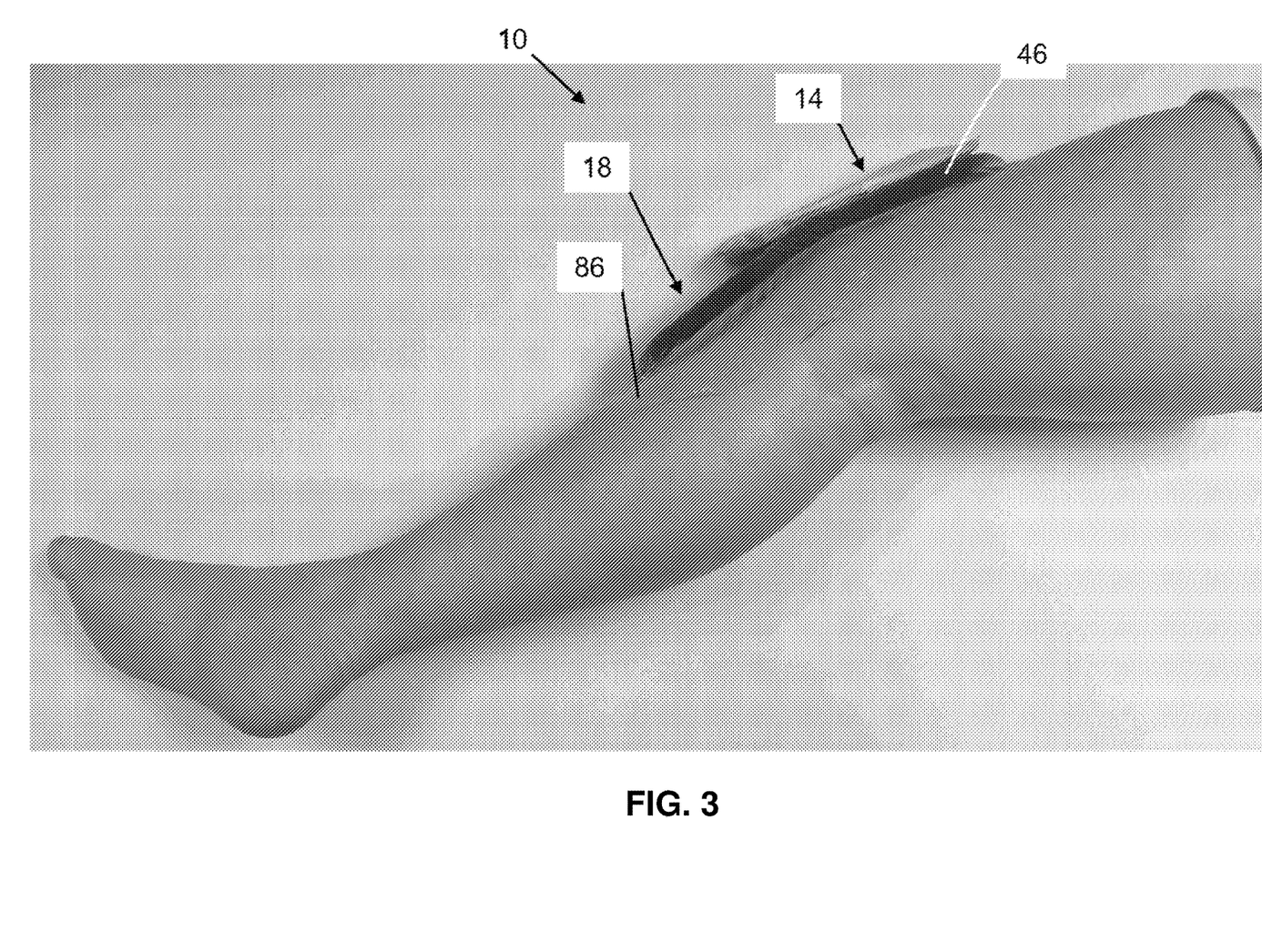
FIG. 3 is a perspective view of the system of FIG. 1 disposed on a model leg.

Referring now to FIGS. 1 and 2, dressing 18 can include a patient-interface layer 30 configured to be in contact with target tissue 22 and/or tissue 26 surrounding the target tissue. For example, patient-interface layer 30 is configured to be disposed below one or more manifolds (e.g., 46). Patient-interface layer 30 can comprise an adhesive configured to couple the patient-interface layer to target tissue 22 and/or tissue 26 surrounding the target tissue. Such an adhesive can be configured to have low tack properties to minimize patient discomfort and/or tissue trauma as a result of the application, repositioning, and/or removal of patient-interface layer 30 from target tissue 22 and/or tissue 26 surrounding the target tissue. Dressing 18 may include a protective liner 34 configured to be disposed on a surface of patient-interface layer 30 such that the protective liner at least partially covers the adhesive (e.g., prior to application of the dressing onto tissue).

Patient-interface layer 30 can comprise a plurality of gas passageways 38 defined by any suitable material, such as, for example, an open-cell foam (e.g., reticulated foam). For example, patient-interface layer 30 can be configured to wick away (e.g., by capillary flow through gas passageways 38) exudate from target tissue 22 and/or tissue 26 surrounding the target tissue. Patient-interface layer 30 can also comprise a plurality of openings 42 configured to allow communication of oxygen and exudate through the openings.

Patient-interface layer 30 can comprise any suitable material, such as, for example, a polymer, optionally, silicone, a hydrogel, polyvinyl alcohol, polyethylene, a polyurethane, polyether, ethylene vinyl acetate, a copolymer thereof, or a blend thereof. Patient-interface layer 30 can be hydrophilic.

Non-limiting examples of patient-interface layer 30 include Silbione® HC2 products, which are commercially available from Bluestar Silicones International, of Lyon, France, Nanova™ Dressing Perforated Silicone Wound Contact Layers, which are commercially available from Kinetic Concepts, Inc., of San Antonio, Texas, USA, and Bioflex® Performance Materials, which are commercially available from Scapa Healthcare of Windsor, Connecticut, USA.

Dressing 18 can include one or more manifolds 46. Each manifold 46 can be configured to allow communication of oxygen to target tissue 22 and/or allow communication of exudate to a sorbent material (e.g., 82) (as discussed in further detail below). Upon application of negative pressure to manifold 46, the manifold is configured to bolster target tissue 22.

Manifold 46 may be porous. For example, each manifold 46 can define a plurality of gas passageways 50 to distribute oxygen across the manifold and/or to collect exudate from target tissue 22 across the manifold. Plurality of gas passageways 50 of each manifold 46 can be interconnected to improve distribution and/or collection of fluids across the manifold. For example, gas passageways 50 can be defined by an open-cell foam (e.g., reticulated foam), tissue paper, gauze, a non-woven textile (e.g., felt), and/or the like. In embodiments where manifold 46 comprises a non-woven textile, dressing 18 can comprise two or more manifolds 46 (e.g., one or more on opposing sides of a sorbent layer (e.g., 78)).

Figure 4:
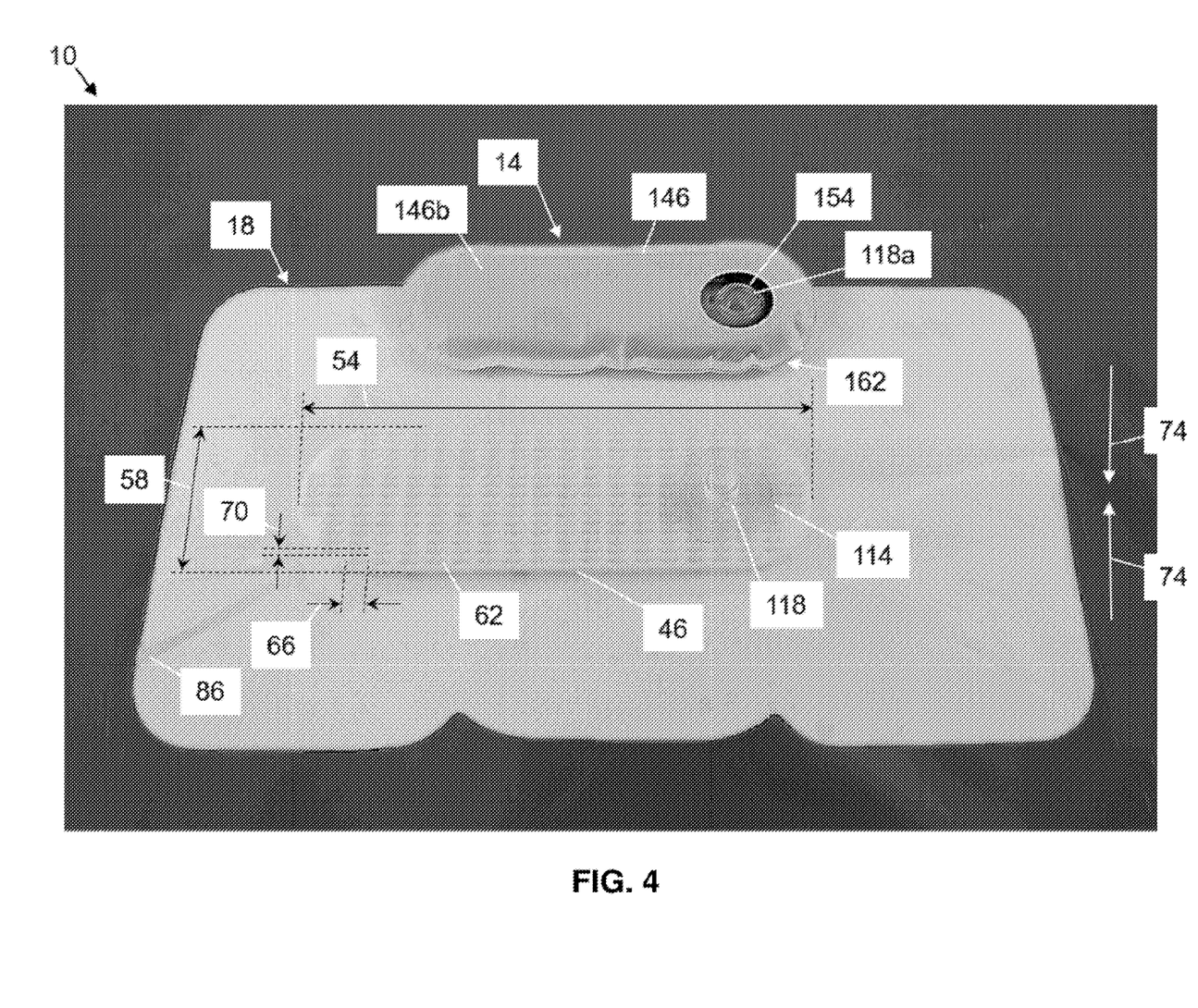
FIG. 4 is perspective view of the system of FIG. 1, shown with a therapy housing of the system of FIG. 1 decoupled from a wound dressing of the system of FIG. 1.

As shown in FIG. 4, manifold 46 can comprise a length 54 and a width 58 that is at least 50 percent less (e.g., 50, 55, 60, 65, 70, 80, 85, 90, or 95 percent less) than the length. Similarly, manifold 46 can define a plurality of openings 62, one or more of which comprises a length 66 and a width 70 that is at least 50 percent less (e.g., 50, 55, 60, 65, 70, 80, 85, 90, or 95 percent less) than the length. Openings 62 of manifold 46 may be formed by a laser or die-cut process that introduces prescribable defects in the bulk of the material of manifold. At least by configuring widths 58 and 70 to be at least 50 percent less than lengths 54 and 66, respectively, and/or due to the prescribable defects within the bulk of the material of manifold 46, when negative pressure is applied to the manifold, the manifold tends to contract in a direction 74 that is substantially parallel to the width of the manifold. Dressing 18, and thus manifold 46, can be configured and/or applied onto target tissue 22 and/or tissue 26 surrounding the target tissue such that length 54 of the manifold and/or length 66 of each opening 62 extends in a direction that is substantially parallel relative to at least a portion of a wound. In this way and others, the contraction of manifold 46 in direction 74 in response to the application of negative pressure can beneficially provide an apposition force onto target tissue 22, which urges opposing sides of a wound toward each other. In some embodiments, a dressing (e.g., 18) can include one or more wound closure strips configured to be applied across an incision such that the strip urges tissue on opposing sides of a wound toward each other. Such wound closure strips can comprise an elastic polymeric material. In at least this way, an apposition force can be applied to an incision without the application of negative pressure.

In instances where apposition forces are undesirable, manifold 46 can have a reduced volume of material, such as, for example, a lower volume non-woven textile or a spacer fabric, which can minimize or eliminate apposition forces applied to target tissue 22.

Manifold 46 can comprise any suitable material, such as, for example, polyethylene, a polyolefin, a polyether, polyurethane, a co-polyester, a copolymer thereof, or a blend thereof. For example, in embodiments where manifold 46 comprises a foam, such a foam may be polyether-based polyurethane foam. Further, in embodiments where manifold 46 comprises a foam, such a foam can comprise a porosity ranging from approximately 20 to 120 ports per inch (ppi), such as, for example, 45 ppi, and a thickness ranging from approximately 2 mm to 12 mm, such as, for example, 6 mm. In embodiments where manifold 46 comprises a non-woven textile, such a non-woven textile can comprise a density ranging from approximately 80 to 150 grams per square meter (GSM) and a thickness ranging from approximately 2 mm to 12 mm.

Non-limiting examples of manifold 46 include MEDISPONGE® Foams, which are commercially available from Essentra PLC of Milton Keynes, England, and Exudate Management Systems, which are commercially available from TWE Group GmbH, of Emsdetten, Germany.

Dressing 18 can include a sorbent layer 78. Sorbent layer 78 can include a sorbent material 82 configured to draw exudate away from target tissue 22 and/or tissue 26 surrounding the target tissue.

As shown in FIGS. 1 and 2, sorbent layer 78 can be configured to be disposed above patient-interface layer 30. Sorbent material 82 can be disposed below or above one of manifolds 46 to capture exudate. As shown in FIGS. 1 and 2, sorbent material 82 can be disposed between a first one of manifolds 46 and a second one of the manifolds. Sorbent layer 78, and, more particularly, sorbent material 82, can comprise any suitable adsorbent or absorbent material. Sorbent layer 78 having absorbent material may comprise a hydrophilic material. Suitable examples of an absorbent material (e.g., a material that tends to swell, by 50 percent or more, due to the binding of liquid within the material) includes a foam, a non-woven textile, a superabsorbent polymer, and/or the like. For example, sorbent material 82 having absorbent material may comprise sodium carboxymethyl cellulose (NaCMC) fiber, alginate fiber, and/or the like. Suitable examples of an adsorbent material (e.g., a material that has a surface onto which liquid binds such that the material does not swell) include carbon filters, such as, for example, an activated charcoal filter and/or the like. Such an activated charcoal filter can be configured to remove nitrogen from oxygen supplied from an oxygen source (e.g., 170) into dressing 18. In this way and others, sorbent material 82 can facilitate the filtration of nitrogen within an interior volume (e.g., 90) of dressing 18.

Non-limiting examples of sorbent material 82 include superabsorbent wound care laminates having a density of 300 grams per square meter (GSM), which are commercially available from Gelok International of Dunbridge, Ohio, USA, and Absorflex™, which has a density of 800 GSM and is commercially available from Texsus S.p.A. of Chiesina Uzzanese, Italy.

In some embodiments, a dressing (e.g., 18) can comprise a liquid control layer that is configured to restrict communication of exudate toward the target tissue. Such a liquid control layer can comprise a plurality of perforations configured to permit exudate to flow away from target tissue 22 through the perforations and block the flow of exudate toward the target tissue through the perforations. Such a liquid control layer can be configured to be disposed between manifold 46 and sorbent layer 78 such that the liquid control layer prevents the backflow of exudate from the sorbent layer to the manifold.

Dressing 18 can include a gas-occlusive layer 86. Gas-occlusive layer 86 can be configured to be disposed over one or more manifolds 46 and coupled to tissue 26 surrounding target tissue 22 such that an interior volume 90 containing the manifold(s) is defined between the gas-occlusive layer and the target tissue and such that the gas-occlusive layer limits the escape of oxygen and/or exudate from the interior volume between the gas-occlusive layer and the tissue surrounding the target tissue.

As shown in FIG. 1, gas-occlusive layer 86 can be configured to be disposed over sorbent layer 78 such that interior volume 90 contains the sorbent material. In other words, sorbent layer 78, and thus, sorbent material 82, can be configured to be disposed below gas-occlusive layer 86. A tissue-facing surface of gas-occlusive layer 86 can comprise an adhesive, such as, for example, an acrylic adhesive, polyurethane gel adhesive, silicone adhesive, a combination thereof, and/or the like, configured to couple the gas-occlusive layer to patient-interface layer 30 and/or tissue 26 surrounding target tissue 22.

Gas-occlusive layer 86 can be sterile such that the gas-occlusive layer provides a viral and/or bacterial barrier to target tissue 22. Gas-occlusive layer 86 may comprise a flexible film, such as, for example, a hydrocolloid sheet. Gas-occlusive layer 86 can comprise any suitable material that limits escape of oxygen and/or exudate through the gas-occlusive layer, such as, for example, polyurethane, polyethylene, polyvinyl acetate, polyvinyl chloride, polyvinylidene chloride, isobutylene, a halogenated isomer (e.g., chlorobutyl and/or bromobutyl), epichlorohydrin, a copolymer thereof, or a blend thereof. Gas-occlusive layer 86 can comprise a thickness that is approximately any one of, or between approximately any two of the following: 5, 10, 15, 20, 25, 30, 35, 40, 45, 50, 55, and 60 micrometers.

Dressing 18 can comprise a valve 94 coupled to gas-occlusive layer 86. Valve 94 can be configured to permit communication of gas out of interior volume 90 through the valve and prevent communication of gas into the interior volume through the valve. For example, valve 94 can be configured to relieve pressure within interior volume 90 when the pressure within the interior volume exceeds a threshold pressure. Such a threshold pressure may range from 8 to 24 mmHg (e.g., approximately any one of, or between approximately any two of the following: 8, 10, 12, 14, 16, 18, 20, 22, and 24 mmHg). Valve 94 can comprise any suitable one-way valve, such as, for example, a ball-check valve, a thin film valve, a diaphragm check valve, and/or the like. In this way and others, valve 94 can be configured to ensure that interior volume 90 does not become over-pressurized with oxygen such that dressing 18 and tissue 26 surrounding target tissue 22 separate to allow oxygen therebetween.

Dressing 18 may comprise one or more sensors 98 configured to collect data indicative of the presence, volume, and/or concentration of oxygen within interior volume 90. Sensor 98 can comprise a material 102 configured to be disposed within interior volume 90. Material 102 can be configured to change color in response to a change in concentration of oxygen within the interior volume. For example, material 102 of sensor 98 can comprise a pressure-sensitive paint, a redox indicator (e.g., comprising methylene blue, phenosafranine, indigo carmine, resazurin, N-phenylanthranilic acid, and/or neutral red). In some embodiments, a sensor (e.g., 98) can comprise a layered silicate, a cationic surfactant, an organic colorant, and a reducing agent. A non-limiting example of sensor 98 includes the Ageless Eye™ Oxygen Indicator, which is commercially available from Mitsubishi Gas Chemical Company, Inc., of Tokyo, Japan, that is modified to change color in response to oxygen exceeding 20 percent purity. Dressing 18 may comprise one or more sensors 106 configured to collect data indicative of one or more of humidity, wound oxygen tension, and/or exudate pH.

Gas-occlusive layer 86 can comprise one or more openings 110 configured to allow communication of oxygen into interior volume 90 of dressing 18. For example, dressing 18 may comprise one or more ports 114, each of which are configured to be coupled to a respective opening 110 of gas-occlusive layer 86 or defined by the gas-occlusive layer. Port 114 can be configured to permit communication of oxygen into interior volume 90 through the port and permit communication of exudate out of the interior volume through the port.

Port 114 may comprise an adhesive configured to seal around opening 110 of gas-occlusive layer 86 in order to minimize the diffusion of oxygen between the port and the gas-occlusive layer.

Port 114 is configured to be releasably coupled to a port (e.g., 154) of housing 14. For example, port 114 can comprise one or more latching and/or interlocking features 118 configured to interact with corresponding latching and/or interlocking features (e.g., 118a) of a port (e.g., 154) of housing 14 such that the port of dressing 18 can be releasably coupled to the port of the housing.

A non-limiting example of port 114 includes the T.R.A.C.™ Pad, which is commercially available from Kinetic Concepts, Inc., of San Antonio, Texas, USA.

Port 114 can comprise a filter 122 to filter fluid that flows through the port. In this embodiment, dressing 18 comprises a filter 122 configured to filter fluid that flows through opening 110 of gas-occlusive layer 86. For example, filter 122 can be sterile such that the filter provides a viral and/or bacterial barrier. As shown in FIGS. 1 and 2, filter 122 comprises a layer of material that is bonded to a lower (e.g., tissue-facing) surface of gas-occlusive layer 86. In some embodiments, a filter (e.g., 122) comprises a layer of material that is bonded to an upper surface of a gas-occlusive layer (e.g., 86). Filter 122 can comprise any suitable material, such as, for example, polytetrafluoroethylene (PTFE) (e.g., an expanded PTFE), a polyester, a polyamide, polyolefin, a copolymer thereof, a blend thereof, and/or the like. Filter 122 can have a backing material, such as, for example, a non-woven textile, comprising a polyester, a polyamide, and/or the like. Filter 122 may comprise a hydrophobic material. To illustrate, filter 122 can be configured to allow communication of oxygen into interior volume 90 through opening 110 of gas-occlusive layer and restrict communication of exudate out of the interior volume through the opening of the gas-occlusive layer.

A non-limiting example of filter 122 includes GORE® Microfiltration Media for Medical Devices, which is commercially available from W. L. Gore & Associates, Inc., of Newark, Delaware, USA.

As shown in FIG. 1, dressing 18 can optionally comprise an oxygen source 126 disposed within interior volume 90. In this embodiment, oxygen source 126 can comprise an oxygen-generating material 130 configured to release oxygen (e.g., a gas whose composition is approximately 99 or more percent oxygen) when exposed to water. Water, in this context, includes any substance having $H_2O$, such as, for example, liquid water, water vapor, and/or other substances that include water, such as, for example, exudate from target tissue 22. Oxygen-generating material 130 can comprise an adduct of hydrogen peroxide, such as, for example, sodium percarbonate and/or hydrogen peroxide-urea. Dressing 18 can have a liquid source 134 comprising one or more capsules 138 configured to be disposed within interior volume 90. Each of capsules 138 can define a pocket that includes water. In this embodiment, flexion and/or breakage of a portion of at least one of capsules 138 can cause the capsule to release water from within the pocket.

System 10 can be configured to regulate the amount of water exposed to oxygen-generating material 130, thereby preventing oversaturation of the oxygen-generating material and limiting the rate and/or volume of oxygen emission. For example, system 10 can comprise a competitive agent 142 disposed within interior volume 90. Competitive agent 142 can comprise any suitable material that absorbs water, such as, for example, sodium carbonate, bentonite, and/or the like. In some embodiments, a dressing (e.g., 18) can comprise sodium carbonate crystals and/or powder configured to act as a carbon dioxide scavenger to increase the concentration of oxygen within an interior volume (e.g., 90), thereby intensifying the therapeutic effect of the oxygen within the interior volume.

As shown in FIG. 1, housing 14 is outside interior volume 90. Housing 14 comprises a sidewall 146 that defines a chamber 150 configured to be in fluid communication with interior volume. For example, housing 14 comprises port 154, which may be coupled to or defined by sidewall 146. Port 154 and port 114 are configured to be releasably coupled to each other such that housing 14 can be decoupled from dressing 18 without decoupling the dressing from tissue 26 surrounding target tissue 22.

By interlocking port 114 and port 154, the ports are configured to permit communication of fluid between chamber 150 and interior volume 90 through the ports. In this way and others, housing 14 can be removed for maintenance and/or replaced for another housing (e.g., 14) having the same or different therapeutic specifications.

Figure 5:
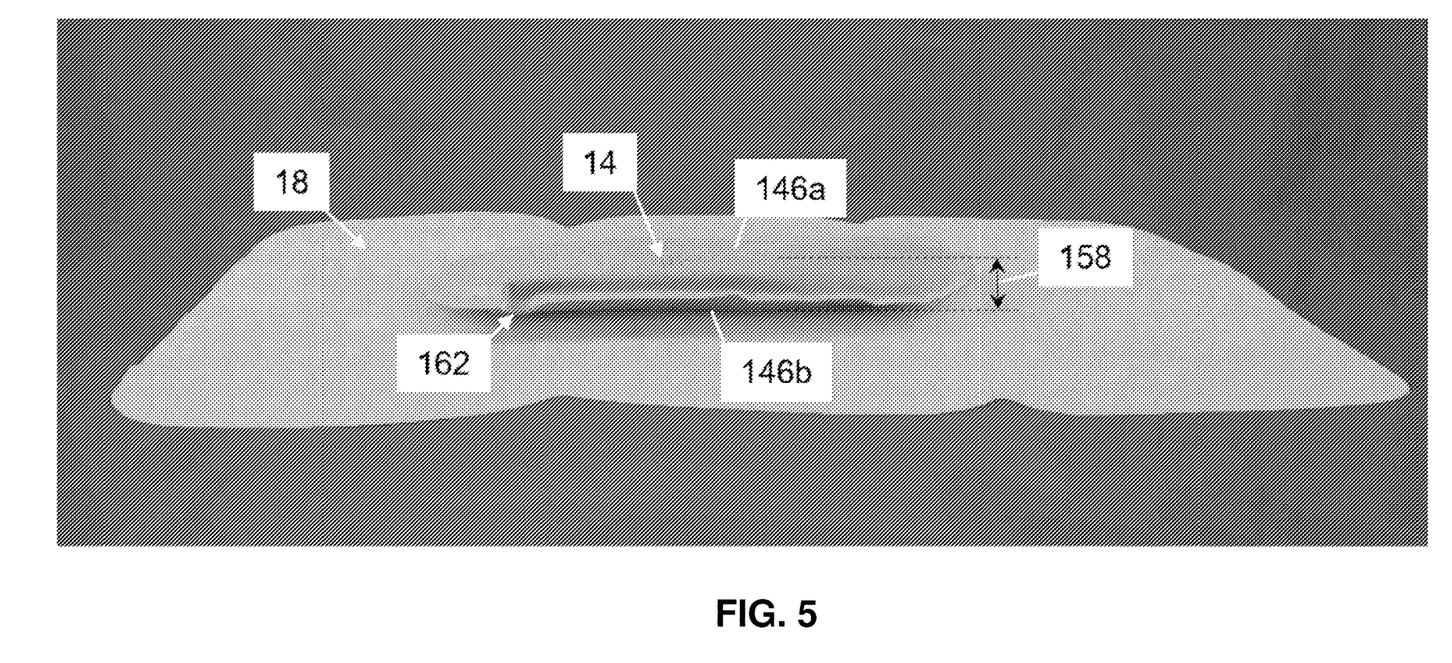
FIG. 5 is perspective view of the system of FIG. 1, shown with the therapy housing of the system of FIG. 1 coupled to the wound dressing of the system of FIG. 1.

As shown in FIG. 5, housing 14 can comprise a thickness 158 extending in a normal direction relative to tissue (e.g., 22 or 26) that is between approximately 5 and approximately 20 mm (e.g., approximately any one of, or between approximately any two of the following: 5, 7.5, 10, 12.5, 15, 17.5, and 20 mm). At least by providing a housing within the range of thicknesses described herein and/or by interlocking a port (e.g., 154) of the housing directly with a port (e.g., 114) of a dressing (e.g., 18), a system (e.g., 10) exhibits a low profile and fits closely along target tissue 22 and/or tissue 26 surrounding the target tissue. Thus, individuals using system 10 can discretely wear the device underneath clothing.

Sidewall 146 of housing 14 may be gas-occlusive. Sidewall 146 can comprise any suitable gas-occlusive material, such as, for example, polyurethane, polyethylene, polyvinyl acetate, polyvinyl chloride, polyvinylidene chloride, isobutylene, a halogenated isomer, a copolymer thereof, or a blend thereof, and/or the like.

Sidewall 146 can comprise a first portion 146a bonded to a second portion 146b such that the first portion and the second portion define a seam 162 therebetween. At least a portion of seam 162 can be configured to allow communication of gas out of chamber 150. For example, at least a portion of seam 162 can be configured to act as a positive exhaust outlet for a negative pressure source (e.g., 166).

Housing 14 can include a negative pressure source 166 disposed within chamber 150. Negative pressure source 166 is configured to be in fluid communication with dressing 18 via ports 114 and 154 such that the negative pressure source can provide negative pressure within interior volume 90 to reduce the volume of the interior volume and/or such that negative pressure is applied to target tissue 22 and/or tissue 26 surrounding the target tissue. In this way and others, negative pressure source 166 improves wound healing and/or improves sealing between dressing 18 and tissue 26 surrounding target tissue 22. As used herein, "negative pressure" can refer to a pressure that is less than a local ambient pressure, such as less than atmospheric pressure.

Negative pressure source 166 can comprise any suitable mechanically and/or electrically-powered device configured to be disposed within and/or coupled to chamber 150, such as, for example, a micro-pump (e.g., a piezoelectric disc pump), a diaphragm pump, a rotary vane pump and/or the like.

Housing 14 can comprise an oxygen source 170 disposed within chamber 150. Oxygen supplied by oxygen source 170 can comprise a high oxygen concentration, such as an oxygen concentration of at least 80 percent (e.g., 80, 85, 90, 92, 94, 96, 98, 99, 99.9, 99.99 or more percent). Oxygen source 170 is configured to be in fluid communication with interior volume 90 such that the oxygen source provides oxygen to the interior volume at a volumetric flow rate ranging from approximately 3 milliliters per hour (mL/hr) to approximately 50 mL/hr (e.g., approximately any one of, or between any two of, the following: 3, 4, 5, 10, 20, 25, 30, 35, 40, and 50 mL/hr).

Oxygen source 170 can comprise any suitable device configured to supply oxygen to dressing 18 at one or more of the volumetric flow rates and/or oxygen concentrations described herein, such as, for example, an electrolytic oxygen source (e.g., an oxygen concentrator). In embodiments where oxygen source 170 comprises an oxygen concentrator, the oxygen source may be configured to remove nitrogen from air (e.g., via one or more filters and/or sieve beds).

Housing 14 can comprise a power source 174 disposed within chamber 150 and configured to provide power to actuate negative pressure source 166 and/or oxygen source 170. Power source 174 can comprise one or more primary cell batteries 178 and/or one or more secondary cell batteries 182. Secondary cell battery 182 can be configured to be inductively charged through sidewall 146 of housing 14 such that the housing minimizes the number of openings in communication with chamber 150. For example, housing 14 may comprise one or more magnets within chamber 150 configured to guide and/or assist in the inductive charging of secondary cell battery 182.

System 10 may comprise a controller 186 (e.g., a processor) configured to control the power provided by power source 174 to negative pressure source 166 and/or oxygen source 170, thereby controlling the negative pressure provided by the negative pressure source and/or controlling the flow rate and/or concentration of oxygen provided by the oxygen source. For examples, controller 186 can be configured to titrate and/or modify levels of oxygen provided by oxygen source 170 based on an individual's wound condition and/or progression of therapy. For example, for wounds created in medical procedures, levels of oxygen and/or reactive oxygen species ("ROS") required in the immediate post-operative period may be greater than levels of oxygen and/or ROS required as time passes after the procedure. Thus, controller 186 can ensure that the intended levels of oxygen and/or ROS are provided at the intended time.

As shown, controller 186 can be located within chamber 150 and may be wired or wirelessly coupled to negative pressure source 166 and/or oxygen source 170. Controller 186 may be configured to be wirelessly operated from a second controller outside of chamber 150, such as, for example, a smartphone, a tablet, a personal computer, and/or the like. Housing 14 can include one or more user control and/or feedback interfaces 190 (e.g., LEDs, knobs, buttons, haptic communication devices, speakers, and/or the like) electrically connected to controller 186 and configured to provide information regarding the operation of system 10, including the level of negative pressure applied within interior volume 90, the flow rate of oxygen being provided by the oxygen source, the existence of any leaks, data collected by sensors 98 and 106, and/or the like. Interface(s) 190 may be configured to wirelessly communicate with a second controller outside of chamber 150, such as, for example, a smartphone, a tablet, a personal computer, and/or the like, to provide information regarding the operation of system 10.

Some embodiments of the present methods comprise coupling one of the present dressings (e.g., 18) to a patient's tissue (e.g., 22 and/or 26); and coupling a housing (e.g., 14) to the dressing, wherein the housing comprises: a sidewall (e.g., 146) that defines a chamber (e.g., 150) configured to be in fluid communication with an interior volume (e.g., 90); an oxygen source (e.g., 170) disposed within the chamber, the oxygen source configured to be in fluid communication with the interior volume; and a negative pressure source (e.g., 166) disposed within the chamber, the negative pressure source configured to be in fluid communication with the interior volume such that the negative pressure source provides sub-atmospheric pressure within the interior volume.

Some embodiments of the present methods comprise introducing oxygen from the oxygen source into the interior volume. In some embodiments of the present methods, introducing oxygen into the interior volume is performed at a volumetric flow rate ranging from approximately 3 milliliters per hour (mL/hr) to approximately 50 mL/hr. In some embodiments of the present methods, oxygen introduced into the interior volume is at a purity of at least 90 percent. In some embodiments of the present methods, oxygen introduced into the interior volume is produced via electrolysis.

In some embodiments of the present methods, the dressing is configured to include the second oxygen source within the interior volume, the second oxygen source having an oxygen-generating material and the method comprises introducing oxygen from the second oxygen source into the interior volume. In some embodiments of the present methods, oxygen introduced from the second oxygen source into the interior volume is produced by exposing the oxygen-generating material to a liquid. In some embodiments of the present methods, the oxygen-generating material comprises an adduct of hydrogen peroxide. In some embodiments of the present methods, the adduct comprises sodium percarbonate and/or hydrogen peroxide-urea.

Some embodiments of the present methods comprise applying sub-atmospheric pressure within the interior volume. In some embodiments of the present methods, the sub-atmospheric pressure is applied to and oxygen is introduced into the interior volume simultaneously.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A dressing configured to be coupled to tissue to facilitate delivery of oxygen to the tissue, the dressing comprising:
   a patient-interface layer configured to be in contact with the tissue, the patient-interface layer defining a plurality of openings configured to permit communication of oxygen and exudate through the patient-interface layer;
   a first manifold configured to permit communication of oxygen to the tissue, the first manifold defining:
      a plurality of gas passageways; and
      a plurality of openings, one or more of which comprises a length and a width that is at least 50 percent less than the length;
   a second manifold configured to permit communication of oxygen to the tissue, the second manifolding defining:
      a plurality of gas passageways; and
      a plurality of openings, one or more of which comprises a length and a width that is at least 50 percent less than the length;
   a sorbent material configured to be disposed below the first manifold and above the second manifold and to capture exudate; and
   a gas-occlusive layer configured to be disposed over the first manifold and the second manifold and coupled to the tissue such that an interior volume containing the first manifold and the second manifold is defined between the gas-occlusive layer and the tissue and the gas-occlusive layer limits escape of oxygen from the interior volume.

2. The dressing of claim 1, comprising a port coupled to the gas-occlusive layer, wherein the port is configured to be releasably coupled to a port of a housing having a sidewall defining a chamber to permit communication of fluid between the chamber and the interior volume through the ports.

3. The dressing of claim 2, comprising a filter configured to filter fluid that flows through the port, wherein the filter:
    includes a layer of material that is bonded to an upper surface or a lower surface of the gas-occlusive layer; and
    is configured to permit communication of oxygen into the interior volume through the port and restrict communication of exudate out of the interior volume through the port.

4. The dressing of claim 2, comprising a valve coupled to the gas-occlusive layer and configured to relieve pressure within the interior volume when pressure within the interior volume exceeds a threshold pressure.

5. The dressing of claim 1, comprising an oxygen source disposed within the interior volume, the oxygen source having an oxygen-generating material configured to release oxygen when exposed to a liquid.

6. The dressing of claim 5, comprising a competitive agent disposed within the interior volume, the competitive agent configured to limit the communication of oxygen to the tissue.

7. The dressing of any of claim 5, wherein the interior volume includes one or more capsules, each of which defines a pocket that includes a liquid.

8. The dressing of claim 1, comprising a sensor configured to detect a presence of oxygen within the interior volume, wherein the sensor comprises a material configured to be disposed within the interior volume and to change color in response to a change in oxygen concentration within the interior volume.

* * * * *